United States Patent [19]
Wyatt

[11] Patent Number: 4,541,719
[45] Date of Patent: Sep. 17, 1985

[54] METHOD AND APPARATUS FOR CHARACTERIZING MICROPARTICLES AND MEASURING THEIR RESPONSE TO THEIR ENVIRONMENT

[76] Inventor: Philip J. Wyatt, 820 E. Haley St., P.O. Box 3003, Santa Barbara, Calif. 93130

[21] Appl. No.: 403,340

[22] Filed: Jul. 20, 1982

[51] Int. Cl.$^4$ ............................................. G01N 21/00
[52] U.S. Cl. ..................................... 356/343; 364/555
[58] Field of Search ............... 356/336, 339, 341, 342, 356/343; 250/574; 364/555, 574, 575

[56] References Cited

U.S. PATENT DOCUMENTS

| | | |
|---|---|---|
| 3,928,140 | 12/1975 | Wyatt et al. . |
| 4,070,113 | 1/1978 | Frazer et al. ......................... 356/343 |
| 4,101,383 | 7/1978 | Wyatt et al. . |
| 4,174,952 | 11/1979 | Cannell et al. ................... 356/341 X |
| 4,204,837 | 5/1980 | Sternberg et al. ............... 356/341 X |
| 4,314,347 | 2/1982 | Stokely ................................ 364/574 |

FOREIGN PATENT DOCUMENTS 1389247  4/1975  United Kingdom ................. 250/574

*Primary Examiner*—Davis L. Willis
*Assistant Examiner*—Matthew W. Koren

[57] ABSTRACT

A process and apparatus is disclosed for characterizing an ensemble of microparticles and monitoring their response to environmental factors such as chemically and biologically active agents. The apparatus permits the very accurate measurement of light or radiation intensity scattered by the microparticles at two well-defined scattering angles with respect to the direction of the incident beam. This is achieved by measuring the scattered radiation at two sets of scattering angles each subtending the two defined angles, processing the detected intensities with a computer means to remove spurious data arising from artifacts in the scattering ensemble, and then functionally averaging the so-processed intensities of each set to yield a mean value for the scattered intensity at each of the two defined angles. Monitoring these two values before and after the addition of an environmental factor permits the calculation of a quantitative ensemble response to said environment. Applications include the quantitative determination of bacterial response to antimicrobials, determination of antigen or antibody concentrations in various fluids, detection of chemical residues in foods and other materials, identification or characterization of unknown particles ensembles by comparison with known scattering values, and detection of bactiurea. Appropriate processes and protocols are disclosed.

34 Claims, 7 Drawing Figures

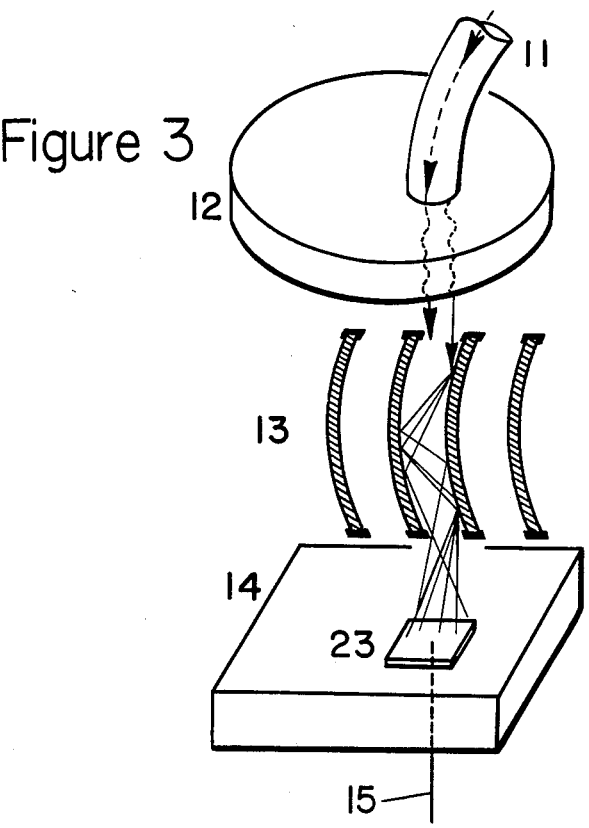
Figure 3
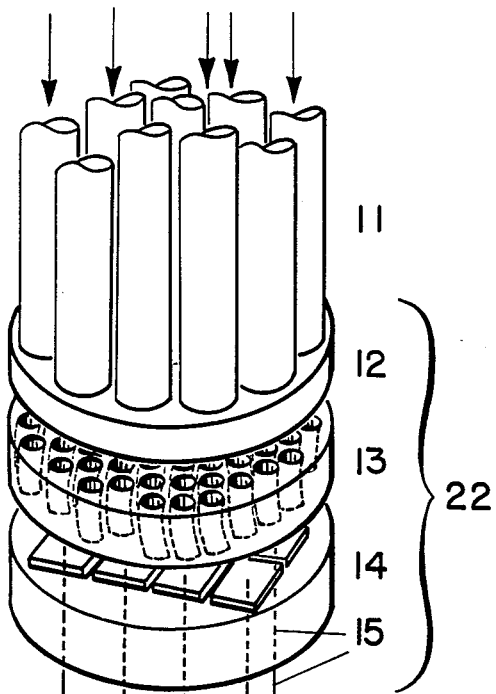
Figure 4
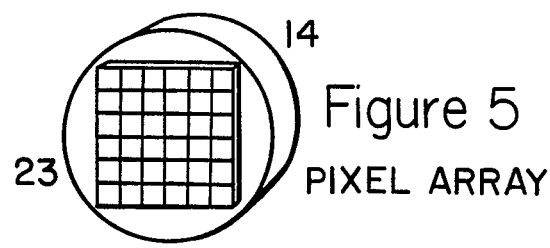
Figure 5
PIXEL ARRAY
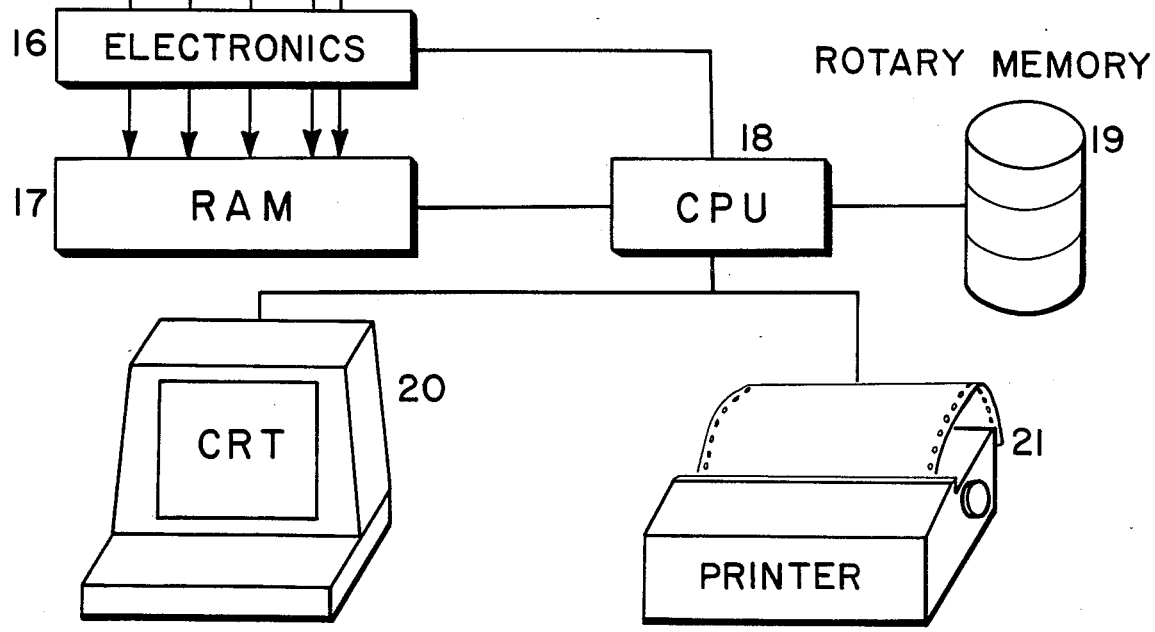

Slope $m_t = (V_{t2} - V_{t1}) / (\Theta_2 - \Theta_1)$

Slope $m_o = (V_{o2} - V_{o1}) / (\Theta_2 - \Theta_1)$

METHOD AND APPARATUS FOR CHARACTERIZING MICROPARTICLES AND MEASURING THEIR RESPONSE TO THEIR ENVIRONMENT

DEFINITIONS

The term light, as used herein, refers in general to electromagnetic radiation of wavelengths varying from x-rays through the far infrared, i.e. a range from a few nanometers to about 50,000 nanometers.

The term microparticle, as used herein, includes but is not limited to a microparticle of organic or inorganic origin such as dust, smog particles, bacterial cells, viruses, antibodies, antigens, pollen, water droplets, liquid droplets, salt crystals, asbestos fibers, platelets, and mammalian cells such as white and red blood cells and squamous cells, and platelets.

The term small particle shall mean microparticle.

The term characterization shall mean identification or classification. The term shall also mean a property derivable from light scattering measurements on which basis the particle or particles so-examined will yield a fingerprint or similar reproducible result, either absolute or relative to a standard, from which the particles may be tagged or associated with a known similar group.

The term ensemble of particles shall mean one or more particles.

The term pixel shall mean anode.

BACKGROUND

The characterization of a particle or an ensemble of particles represents an important determination for many industries. For example, in the beverage industry, an objective means by which a particular drink is characterized plays a major role in quality control. Many chemical processes require a controlled particle size distribution and density prior to the initiation of various chemical reactions. This in turn requires some relatively simple means for identifying those size parameters and particle density properties before their introduction into the process itself. Many measurements in the food industry relating to quality control actually have their origin in subjective taste testing. A suitable characterization of the particles giving rise to the particular tastes of importance would result in a simpler and more reproducible test.

The measurement and interpretation of the response of a microparticle to its environment is an important objective of numerous determinations. In the area of immunochemistry, for example, the concentration of antibodies in a patient's serum is generally determined by exposing such antibodies to an environment of antigens specific to them or complexes created from them and monitoring their reaction. For antibiotic chemotherapy studies, bacterial isolates are often exposed to an antibiotic environment to determine the potential effectiveness of such drugs. Effects of temperature and various chemical concentrations on chemical reactions invariably involve similar measurement techniques.

The presence of adulterants and/or toxicants in food and water supplies are generally detected by means of particles, including molecules, which undergo significant physical changes in their environment. There are at present several methods by which such environmentally-caused changes may be detected and monitored and particles themselves characterized.

Turbidimetric and nephelometric techniques are most prevalent. Such measurements are often used to characterize particle density. Changes in light transmission or the amount of light scattered in a particular direction forms the basis, respectively, of these two methods. Although attractive for their instrumental simplicity, these methods are not particularly sensitive nor accurate because of inherent experimental problems including, but not limited to, high background fluctuations and contributions, light source instabilities, and lack of suitable reference standards.

A method of considerable promise for characterizing particles or measuring their environmental response is that of differential light scattering (DLS) whereby detailed variations of light scattered intensity with angle are measured and recorded. The resulting DLS patterns are then compared to yield a measurement of particle morphological change, as well as number density variations. Comparing with a reference standard can result in a useful particle characterization procedure. The DLS technique requires extensive detection electronics, as well as complex computer interpretation routines. The DLS approach also depends critically upon the shape of the recorded light scattering pattern and its results are very susceptible to small shape changes that may arise from artifacts such as debris or markings/irregularities of the sample holder.

Electrical impedance methods are often used to determine particle size distributions and number densities. Such measurements performed before and after exposure to various environments provide a means for monitoring their response as well as yielding important characterization properties. Particles are suspended in a saline solution and forced through a fine capillary tube across which an electrical potential is applied. As each particle traverses the capillary an impedance change occurs due to the particle physically obstructing the electrical conduction path. The resultant pulse is said to be proportional to the particle's physical cross section. The basic shortcomings of the method include capillary plugging, requiring frequent cleaning, and lack of adequate size resolution below a few micrometers.

Radiometric measurements are of frequent use, especially for immunochemical determinations, yet despite their inherent accuracy, these techniques invariably present the user with problems of waste disposal and health hazards. Numerous other measurement techniques exist for characterizing particles and monitoring their environmental response, including colorimetric reactions, plate diffusion methods, electrochemical impedance changes, and a variety of precipitation techniques.

SUMMARY OF THE PRESENT INVENTION

The present invention uses an optical technique to characterize particles and measure their response to their environment. For measuring environmental response, weighted measurements of scattered light intensity at two distinct angles are compared before and after exposing the particle or particles to an environment that will affect them. By means of simple algorithms, these four values yield a quantitative measure of changes in particle morphology, and particle number density. By means of a reference standard or absolute intensity values, the two numbers corresponding to the measured scattered intensities at the two angles prescribed are used to characterize the particle sample measured against such a reference. In the preferred embodiment of the invention, vertically plane polarized incident radiation is produced by a laser. The pair of angles lie preferably on opposite sides of right angle scattering, corresponding to traditional nephelometry, and their values are weighted by averaging, respectively, over a set of angles subtending each of the two selected. Included in this averaging process is the explicit examination of these data so as to remove data points unequivocably arising from noise sources. In this manner two very precise nephelometric-like measurements are obtained at two distinct angles by measuring scattered light over two distinct sets of angles and weighting each contribution, rather than measuring the scattered light by means of a single optical collector spanning a broad angular range.

The significance of the weighted measurements of the scattered intensities at two distinct angles is straightforward. When particles are extremely small with respect to the wavelength of the incident radiation, they tend to scatter it isotropically. Contributions from larger particles results in a departure from isotropic scattering, with the greater part of the scattered flux being into the forward, small angle, direction. For particles comparable to the size of the incident wavelength, the forward-backward asymmetry can exceed two or even three orders of magnitude. An absolute measurement of light scattered in the forward direction thus gives a measure, or at least an indication, of large particle contributions, whereas a backscattered value is a representation of predominantly small particle contributions. These two values must be very carefully measured and averaged over angles subtending each to preclude intensity value anomalies that might arise at certain angular locations due to possible interference effects. All measurements from an ensemble of particles must be made at sufficient particle dilutions to insure that only single scattering events are contributing. Thus the mean free distance between successive scattering events must be large compared to the dimensions of the cuvettes or vessel containing the particles.

The proposed technique differs from the conventional approach as measurements are made at two distinct angular locations and the measurements at each location are suitably weighted over broad angular ranges or arcs centered about each location. It also differs from the differential light scattering techniques of Wyatt, et al. wherein measurements are obtained at a plurality of angles to derive a so-called DLS pattern whose comparisons also yield morphology and number density changes. The present method does not require the examination of complex patterns to detect changes, but relies instead on much simpler nephelometric determinations selected specifically to improve the accuracy and reproducibility of such measurements.

FIG. 1 presents a schematic picture of the preferred embodiment of the present invention. Two sets of detectors, each member of a set measuring the scattered light intensity from the scattering particles at a discrete angle, are arranged in two arcs about the two selected angles $\Theta_1$ and $\Theta_2$. All detectors are preferably equidistant from the scattering ensemble of particles in the preferred embodiment and all intensity values are, radiation, normalized to the intensity of the incident radiation intensity by means of a beam splitter 5. The $n_1$ measured scattered intensities $I_1(\theta_i)$ ($i=1$ to $n_1$), about arc 1, are each first processed for spurious noise contributions, weighted by operating on each with some functional operator, $W(I_1)$, and then averaged; similarly for arc 2.

On the foregoing basis, two weighted intensity values may be generated from each measurement. Thus if the $n_1$ values measured about $\theta_1$ be $I_1(\theta_1)$, $i=1$ to $n_1$, we form the sum $$S_1 = \frac{1}{n_1} \sum_{i=1}^{n_1} W[I_1(\theta_i)],$$

where W is some weighting function such as a multiplicative constant, $W_i$, possibly varying with each $\theta_1$, or a logarithmic operation, log $[I_1(\theta_i)]$, or any other useful functional operation. Similarly for $\theta_2$, a value $S_2$ may be generated. In order to obtain a quantitative measure of the response of a microparticle or microparticles to an environment, one needs only make measurements to determine $S_{o1}$ and $S_{o2}$ at time $t=0$ before exposure to the environment, and then determing these same quantities at a later time after the system has experienced the environment for a time t, viz. $S_{t1}$ and $S_{t2}$. The four derived nephelometric quantities $S_{o1}$, $S_{o2}$, $S_{t1}$, $S_{t2}$ then combined by an algorithm, provide the basis for a numerical quantitation of the particle system's response to its environment. Similarly, by comparing the parameters $S_{o1}$ and $S_{o2}$ against some reference values $S_{R1}$ and $S_{R2}$, a quantitative characterization of the particle ensemble may be obtained.

BRIEF DESCRIPTION OF THE DRAWINGS

FIG. 3 is a schematic view of a single microchannel showing how a photon incident at the photo-cathode produces a burst of electrons after amplification at the collecting pixel.

FIG. 4 shows the interrelation of the detection electronics and the controlling computer system.

FIG. 5 is a header showing the pixels of the multianode microchannel array.

DETAILED SPECIFICATION OF THE INVENTION

Figure 1:
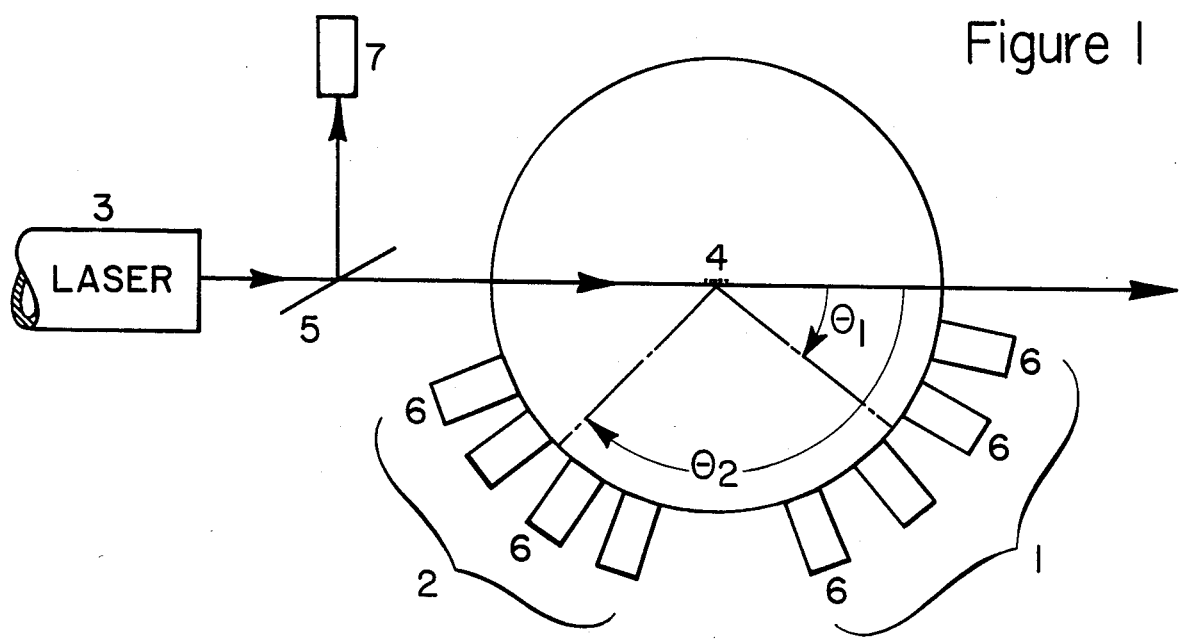
FIG. 1 is a schematic diagram showing the relative placement of the key elements of the measurement setup.
Figure 2:
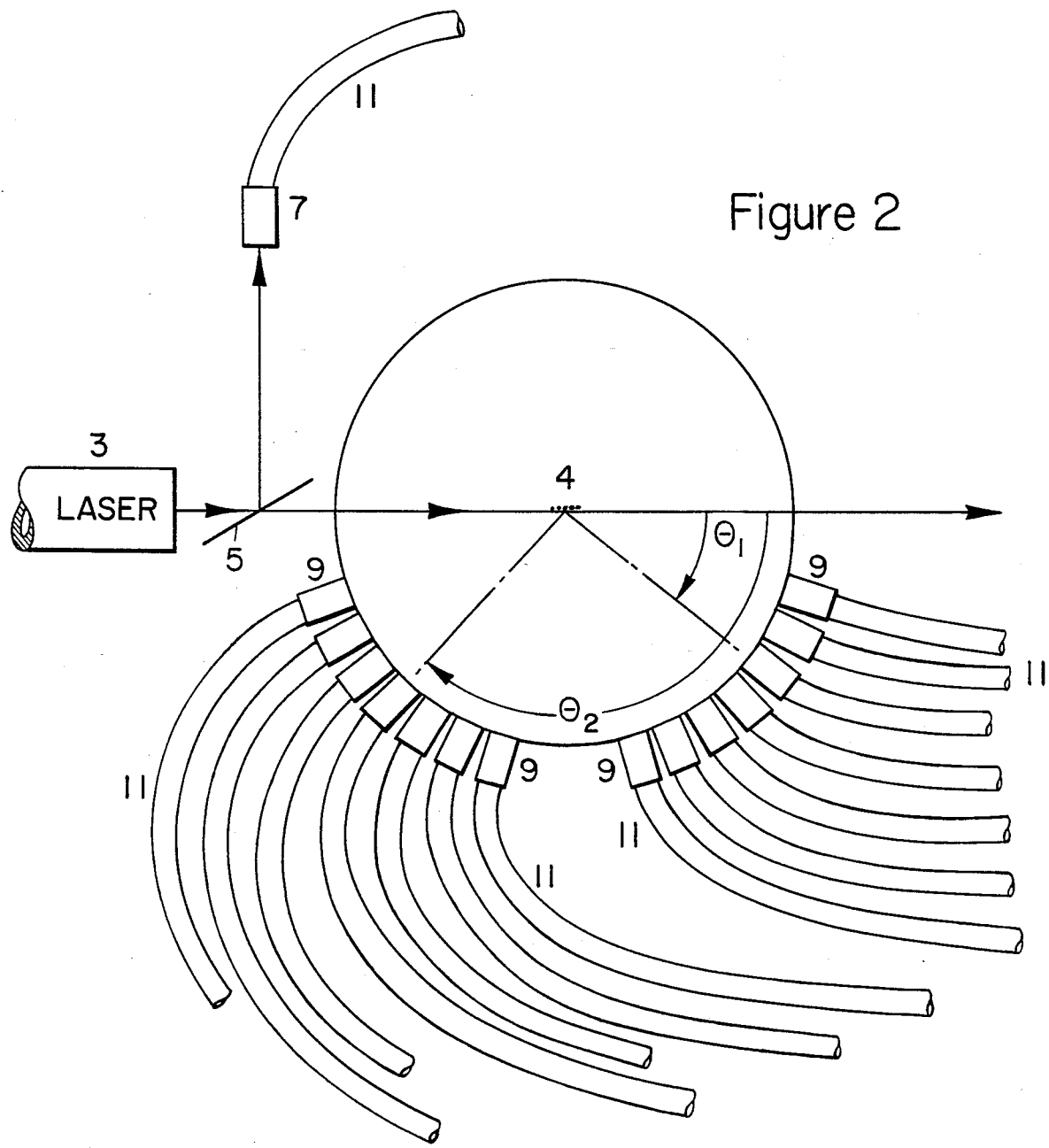
FIG. 2 shows individual detectors of FIG. 1 placed with optical fibers carrying the light signals from all detection locations to detector means.

Referring once more to FIG. 1, the intensity of radiation into angles $\Theta_1$ and $\Theta_2$, respectively, from a scattering system made up of a single particle or an ensemble of particles is determined at each of these angles as follows: An incident, collimated source of radiation 3 illuminates an ensemble of particles 4 which scatter this radiation into all directions. About a particular pair of directions, $\Theta_1$ and $\Theta_2$ are placed a set of detectors 1 and 2, respectively, or means, such as optical fibers connected to radiation sensitive detectors, to permit measurement of the relative scattered radiation intensity at each angular location 6 in the vicinity of the specific angular direction $\Theta_1$ or $\Theta_2$. In the preferred embodiment of this invention, the radiation source would correspond to a laser producing monochromatic visible or infrared radiation, plane polarized vertically with respect to the plane containing the two arrays of detectors 1 and 2, alternatively, the incident radiation could be from an incoherent light source such as mercury arc lamp or a high pressure xenon lamp subsequently collimated to provide a relatively narrow beam on the scattering ensemble of particles. All intensity values detected are normalized by dividing such values by a part of the incident radiation intensity by means of a beam splitter 5 reflecting a normalizing intensity detected at means 7. In addition, the set of detectors around each of the two angles $\Theta_1$ and $\Theta_2$ need not be coplanar, though in the preferred embodiment they would lie on an arc of a circle centered at 4 or on a spherical surface equally centered.

Referring to FIGS. 1, 2, 3 and 4, in place of the two detector array elements 6, two bundles of optical fibers 11 attached by means 9, may be used to transmit the scattered light to the face plate 12 of a multianode microchannel array (MAMA) tube 22 of the type manufactured by Litton Industries and Ball Aerospace Systems Division and as discussed in a co-pending patent application Ser. No. 390,980.

The MAMA tube may be thought of as a set of photomultipliers operating in parallel FIG. 3 shows details of the tube operating principle. Below each attached fiber element 11 corresponding to a particular angular location is a photocathode surface 12 followed by a set of microchannels in the microchannel plate 13. Photoelectrons produced in a local region of the photocathode 12 are accelerated through a microchannel 13 and yield a burst of electrons at a corresponding pixel element 23 in the pixel array 14. In general, a fiber element will subtend a region of the photocathode corresponding approximately to the area of a pixel element 23. Of the order of 30 to 100 microchannels 13 will supply electrons to each pixel. Referring now to FIG. 4, bursts of electrons impinging on each pixel, or anode, are transmitted by the means 15 to amplifying and counting electronics 16 which increments a random access memory RAM counter/word residing in a computer accessible RAM 17. Each pixel provides the counts for its own RAM word. By means of a central processor unit 18, the counters may be read and zeroed under program control. The physical arrangement of the pixels is shown in FIG. 5.

Figure 6:
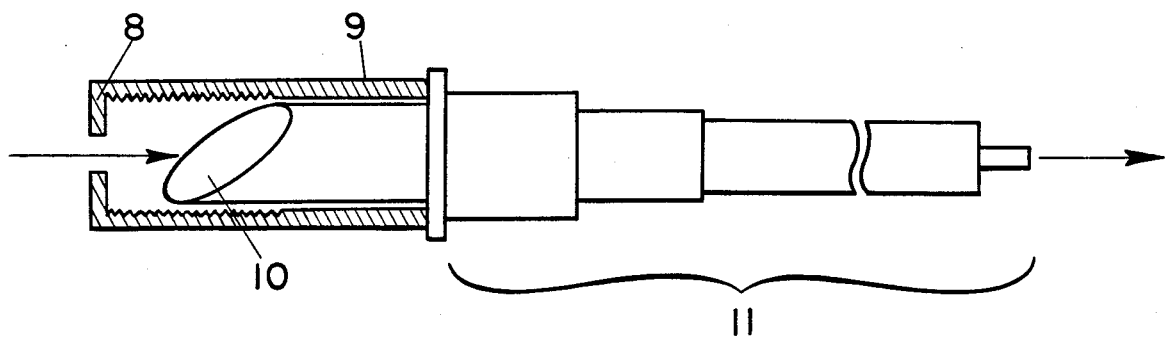
FIG. 6 is the aperture structure attached to an optical fiber.

The pixel counting rates which should be directly proportional to the incident photon flux through the corresponding fiber element usually remain linear up to a few megahertz. If the photon flux from a particular fiber element 11 be too great, the corresponding pixel element 23 would saturate and result in a non linear counting rate thereby distorting the actual intensity value initiating that particular rate. As shown in FIG. 6, by carrying the cross section of the individual fibers 11 or by varying the masks 8 to which they are attached by means 9, the maximum photon flux incident on each fiber element per second may be varied. Because, as has been previously mentioned, as the particles increase in size relative to the wavelength of the incident radiation, the light scattered by them becomes more pronounced in the forward scattering direction. The masks 8 corresponding to the forward detector set 1 would, in the preferred embodiment of this invention be of smaller cross section than those of the corresponding larger scatter angle detector set 2. After counting is completed, the recorded rates may be corrected for the mask-attenuated values. Since photons scattered by the target particles 4 should not reflect from the detecting fiber elements, as these reflections could cause additional noise in the system and degrade the absolute differences derived between forward and backward intensities, the face of each fiber element 10 should be slightly beveled, in the preferred embodiment of this invention, so as to prevent such reflected light from exiting through the mask element 8.

In the preferred embodiment of this invention, the counts of each pixel may be limited to fixed time periods under program control via the central processing unit 18. For some types of measurements, on which basis a particular microparticle ensemble is to be characterized or compared to a reference system, the time periods could be quite long, perhaps corresponding to several seconds, or even minutes. For other types of measurements whereby instantaneous values need be obtained so as to derive effective scattered radiation rates at the two angular positions $\Theta_1$ and $\Theta_2$, the time periods might be chosen as small fractions of a second, depending upon the resolution required. It is important to stress, however, that the intensity or rate values derived from the measurements at the two distinct angular positions $\Theta_1$ and $\Theta_2$ be as free from spurious noise as possible. Between counts it will be necessary for the CPU 18 to analyse the data at each of the satellite angular locations to detect and suppress values whose origins did not correspond to the particular particle ensemble being studied. For example, were one to monitor the reaction rate between interacting antigen-antibody complexes, some contributions to the recorded signals would be expected to arise because of cellular remnants in the serum aliquot used in the experiment, or even dust or debris that may have been inadvertently been introduced into the sample. A significant feature of the angular arrays surrounding the two principal angular locations should now be apparent: by examining the scattered light variations at many angles with respect to the incident beam direction, contributions from specular reflections, as would be expected from large pieces of debris may be easily followed. During time periods in which such anomalous scattering events are taking place, the CPU system of the preferred embodiment should be programmed to suppress the recorded values completely, replacing them with values derived by interpolation of noisefree results spanning in time the noise events.

Although the preferred embodiment of the invention has indicated the use of a compact MAMA tube, with associated electronics, for the initial detection of the angular scattering data, other detection schemes may be equally well adapted as would be evident to those skilled in the art of measuring scattered light intensities. These would include, but not be limited to, sets of photodiodes with appropriate amplifiers as well as groups of photomultipliers, vidicons, and digicon units such as manufactured by SAI, Inc.

It is important to emphasize that the present invention is not a simple variation of a nephelometer, nor is the measurement a variation of a dissymmetry measurement such as performed by physical chemists concerned with the determination of molecular weights or particles sizes. Likewise, it is not similar to the dual angle device of Sloan as discussed in his U.S. Pat. No. 2,816,479. As regards a conventional nephelometer, such an instrument makes a measurement of the scattered light intensity at a fixed angle or collects the total amount of light scattered into a single detector structure spanning a broad angular range. A dissymmetry measurement, on the other hand, usually consists of making a measurement of the ratio of light scattered at 45° to light scattered at 135°. For particles very small compared to the wavelength of the incident light, this ratio is unity. As the particle size increases, the ratio increases thus signifying the presence of larger particles. Many different size distributions, however, can yield identical dissymmetry ratios and for the case of monodisperse particles, once their size becomes comparable to the wavelength of the incident light, the ratio may again be less than unity when sharp scattering minima occur at 45°. By measuring the scattered intensity ratio at two angles near the forward direction, Sloan's device was useful for detecting the presence of particles and obtaining a coarse measurement of their average size.

The present invention makes two absolute measurements of the scattered intensity at two angles: one in the forward direction and one at a larger angle, as has been previously described. Since each of these measurements has been averaged over a range of angles subtending the chosen angles, and since the values at each angle have been processed digitally to remove as many detected spurious data as possible before averaging, the resulting two values will be of such a precise nature that subsequent measurements of the same particulate ensemble under the same physical conditions will yield the same values. Thus these two values referred to the two values of a fixed standard such as a known concentration of polystyrene latex particles as manufactured by Dow Chemical Co., or to some absolute photometric standard, may be used for the absolute characterization of the light scattering ensemble or as a simple means to compare one ensemble with another, or as a means to monitor the response of a microparticle ensemble to its environment, with the aforementioned two values being measured before and after exposure to the environment. Naturally, the means of combining the detected angular data to yield these two averaged values may be of many forms, as has been described previously, such as multiplicative weighting before averaging, forming the logarithms of each processed value before averaging, etc. The particular operation performed on the processed angular scattering data before averaging would naturally depend on the types of particles being considered. In the preferred embodiment of this invention, the instrument performing these measurements would be under program control and would yield intensity values at the two angles based on one or more selected averaging procedures. Indeed, several pairs of output values could be generated following each measurement, one pair for each averaging procedure employed. Thus a given particle ensemble could be characterized by several pairs of numbers, each pair of which is based on a different averaging technique.

As an example of the processing of the recorded data to yield the two scattering values for a particular ensemble of particles, consider that measurements are made at each of the $n_1$ angular locations surrounding angle $\Theta_1$ and each of the $n_2$ angular locations surrounding angle $\Theta_2$. Note that $n_1$ and $n_2$ need not be equal, nor need the spacings between the angular locations be equidistant. At a particular angle $\theta_{i1}$ ($i=1$ to $n_1$), let N successive measurements be made of the scattered intensity $I_{i1}$ within a time period $\tau$ such that the physical properties of the ensemble have not been affected by their environment during this time. Calculate the average value $\overline{I}_{i1}$ and its associated standard deviation $\delta_{i1}$. Discard any value exceeding, say, two standard deviations and recalculate the average value $\overline{I}_{i1}$. Repeat this procedure until all remaining values lie within one standard deviation. Repeat for all the $n_1$ angles $\theta_{i1}$ and the $n_2$ angles $\theta_{i2}$, all intensities measured within the time $\tau$.

Now consider some weighting operator, W, such as a logarithmic operation and/or an arithmetic scaling factor $f_i$, and calculate $W[I_{i1}]f_i$, $i=1$ to $n_1$ and $W[I_{i2}]f_i$, $i=1$ to $n_2$. The average values associated with angle $\Theta_1$ and $\Theta_2$, respectively, would then be given by $$V_1 = \frac{1}{n_1} \sum_{i=1}^{n_1} W[I_{i1}]f_{i1}, \text{ and} \tag{1}$$

$$V_2 = \frac{1}{n_2} \sum_{i=2}^{n_2} W[I_{i2}]f_{i2}. \tag{2}$$

If one now wishes to establish a pair of values characterizing a particular scattering ensemble with respect to some reference values, $V_{1R}$ and $V_{2R}$, one could form the differences $$D_1 = V_{1R} - V_1 \text{ and} \tag{3}$$

$$D_2 = V_{2R} - V_2, \tag{4}$$

and use these values as the characterizing pair.

Figure 7:
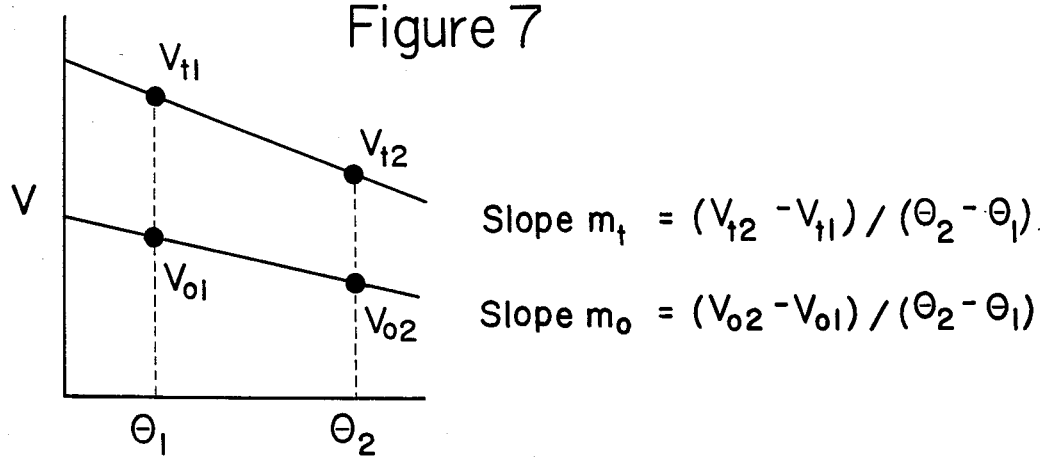
FIG. 7 identifies the mathematical quantities derived from the preferred embodiment of the measurement.

If one wishes to monitor the response of a particle ensemble to its environment, one would measure first the quantities $V_{10}$ and $V_{20}$ corresponding to $V_1$ and $V_2$, respectively, at time $t=0$, i.e. before the particles were exposed to the environment. Then one would measure the corresponding quantities after interacting with the environment for a period of time t, viz. $V_{1t}$ and $V_{2t}$. In the preferred embodiment of the present method, the response, R, of the particles to their environment could be represented quantitatively by $$R = a(V_{10} - V_{1t}) + b(V_{20} - V_{2t}) + c(m_0 - m_t), \tag{5}$$

where a, b, c are constants and $m_0$ and $m_t$ are the slopes, respectively, of the straight lines joining $V_{10}$ to $V_{20}$ and $V_{1t}$ to $V_{2t}$ viz.

$$m_0 = (V_{20} - V_{10})/\Delta\Theta \tag{6}$$

$$m_t = (V_{2t} - V_{1t})/\Delta\Theta, \tag{7}$$

where $\Delta\Theta = \Theta_1$. Note the if W corresponds to the function log, then $F = \frac{1}{2}V_{10} - V_{1t}) + \frac{1}{2}(V_{2t})$ is approximately proportional to 10 g ($n_0/n$) where $n_0$ is the number density of the particles at $t=0$ and n is the number density of particles at time t. This approximation assumes the particle ensembles experience negligible changes in their average size or size distributions in the time interval between 0 and t. The so-called slopes, $m_0$ and $m_t$, represent a functional measure only of the average size of the ensemble at time 0 and t, respectively. The more negative these values become, the larger average particle size would be associated with the corresponding ensemble. The term in Eq. (5) involving $m_0 - m_t$ therefore represents a measure of the change of the ensemble particle size distribution. FIG. 7 illustrates the meanings of $m_0$, $m_t$, $V_{01}$, $V_{02}$, $V_{1t}$, and $V_{2t}$.

For certain environments, one wishes to compare the response, $R_c$, of a control ensemble of particles which do not experience the environment with the response, $R_T$, of a test ensemble exposed to the environmental stress. Referring to the example of a response given by Eq. (5), one would generate it for the control ensemble to yield $R_c$ and then for the test ensemble to yield $R_T$. There are two important examples of the utility of this type of determination.

First consider the measurement of the response of an ensemble of bacterial cells isolated from an infection site to a particular antimicrobial agent. Two identical aliquots of the bacterial cells are placed in separate identical cuvettes containing some type of growth medium such as Columbia broth. To one is added a certain concentration of the antimicrobial under consideration; to the other is added an equal fluid volume, absent the antimicrobial. Both final solutions have the same initial bacterial concentrations an at time $t=0$, the quantities $V_1$ and $V_2$ are identical since the set $I_{i1}$ ($i=1$ to $n_1$) and $I_{i2}$ ($i=1$ to $n_2$) are identical for both solutions. Any departures from equality at $t=0$ immediately may be used to warn of a misprepared sample or malfunctioning detection means. After incubation for a period of time t, measurements of $V_1$ and $V_2$ for the control sample will differ from measurements of $V_1$ and $V_2$ for the test sample, if the antimicrobial has had an effect. In this case, the responses $R_c$ and $R_T$ will be different. These responses may now be used to quantitate the minimum inhibitory concentration, or simply MIC, by calculating a functional quantity, $M(R_c, R_T, D)$, where D is the concentration of the antimicrobial yielding this difference between the responses $R_c$ and $R_T$. For example, the function M yielding an MIC value might be simply of the form:

$$M = \frac{aD}{R_C - R_T} \quad (8)$$

where a is a constant, usually depending on the type of antimicrobial tested. The form of Eq. (8) shows that for a given concentration, D, the less the effect of the antimicrobial, the greater is the expected MIC, since $R_T \to R_c$ as the antimicrobial effect diminishes.

Consider next the case where viable bacterial cells, for example, are to be used in a bioassay test for the presence of some type of toxicant in a solution, such as water. To a control sample of an equivalent solution known a priori to contain no toxicant is added an aliquot of the bacteria. An equal aliquot of cells is added to the test solution. If the latter contain a toxicant to which the test bacteria are sensitive, then after incubation, the measured response to the sample solution will differ from the response to the control solution. This difference represents therefore an indication that the test solution contains a toxicant or other substance that affects the test bacteria, i.e. the method yield a bioassay of the sample solution for the range and levels of toxicants to which the test organisms are responsive. Similar examples of such bioassay procedures would include, but not be limited to, the bioassay of various food exudates for the presence of residues such as herbicides, antimicrobials, pesticides, mycotoxins, and heavy metals.

The characterization of particle ensembles by measurement of the quantities $V_1$ and $V_2$ or $D_1$ and $D_2$ permits, under suitable conditions, the detection of specific particle ensembles for which such characterization parameters are unique. For example, consider the detection of bacteria in urine, a potentially life threatening infection referred to as bactiurea. With the exception of some white and, possibly, red blood cells, large crystalline precipitates, and other agglomerates, urine is sterile and generally free of particles. By coarse filtering, all of the larger particles, say greater in diameter than 3 μm, may be easily removed. If the remaining filtrate contains bacteria at a sufficient concentration to scatter a sufficient fraction of the total incident light scattered, then the presumptive detection of such cells may be made if the data $V_1$ and $V_2$ fall in certain prescribed ranges. Confirmation of the presence of bacteria or yeasts and quantitation of the number densities present may be implemented by measuring a response function of the type of Eq. (5) over various periods of time, while monitoring values of $V_{1t}$ and $V_{2t}$ to further confirm that these values do indeed lie within ranges characteristic of bacteria or yeasts.

It will be appreciated that any toxicants or other chemical agents to which a strain of bacteria may be found sensitive/responsive may be detected and assayed by the above described procedures.

While there have hereinbefore been presented what are at present considered to be the preferred embodiment and method, it will be apparent to those of ordinary skill in the art that many modifications and variations may be made therefore without departing from the true spirit and scope of the invention. All such variations and modifications, therefore, are considered to be a part of the invention.

What is claimed is:

1. A process for characterizing an ensemble of microparticles comprising the steps of:
   A. preparing a sample of said particles;
   B. illuminating said particles with a beam of radiation from a radiation source;
   C. measuring over a fixed period of time the intensities of radiation scattered by said particles at two sets of discrete scattering angles with respect to the direction of the incident beam, each set of angles substending a range about each of two given angular directions;
   D. examining the variations of scattered intensity at each angular location with smaller intervals of such fixed time period and eliminating those values corresponding to large fluctuations from the mean value calculated during said fixed time period;
   E. calculating the means scattered intensity value at each angular location member of each of the two sets of angular directions;
   F. forming at least a first mathematical average scattered intensity of each set by combining the individual mean intensities of each element of the set yielding two characterizing values;
   G. comparing said two characterizing values with two reference values to yield two values characterizing the particle ensemble.

2. A process for identifying an unknown particle ensemble by performing the measurements of claim 1 and comparing the two characterizing values so obtained with a set of known characterizing values to yield a most probable identification.

3. The process of claim 1 where the intensities are measured by detectors lying in a plane.

4. The process of claim 1 where the incident radiation is produced by a laser at visible or infrared optical wavelengths.

5. The process of claim 1 where said first mathematical average scattered intensity V of each set containing n intensity values is of the form $$V = \frac{1}{n} \sum_{i=1}^{n} W(I_i) f_i$$

where W is a first weighting function of the intensity $I_i$ measured at angular location $\theta_i$ and $f_i$ is a first weighting factor associated with said measured value $I_i$.

6. The process of claim 5 where W corresponds to the logarithmic operation.

7. A process for characterizing an ensemble of microparticles comprising the process of claim 5 repeated N additional times using N additional weighting functions $W_k$, k=1 to N, and corresponding weighting factor sets $f_i$ to yield N additional V-values for each of the two angle sets; said first and N additional V-values providing a set of 2(N+1) characterizing values.

8. A process for detecting the presence of specific microparticles within a sample comprising the steps of:
   A. preparing a sample to be tested;
   B. performing the measurement of claim 1 to yield two values characterizing the sample;
   C. comparing said values with the expected values corresponding to those of the microparticles to be detected;
   D. deducing that said microparticles exist in the sample as said sample has produced the two values characteristic of said particles to be detected.

9. The process of claim 8 where the sample is a urine specimen and the microparticles are bacteria or yeasts.

10. A process for measuring the response of a microparticle ensemble to its environment comprising the steps of:
   A. preparing a sample of said microparticles;
   B. illuminating said particles with a beam of radiation from a radiation source;
   C. measuring over a fixed period of time the intensities of radiation scattered by said particles at two sets of discrete scattering angles with respect to the direction of the incident beam, each set of angles subtending a range about each of two given angular directions;
   D. examining the variations of scattered intensity at each angular location within smaller intervals of such fixed time period and eliminating those values corresponding to large fluctuations from the mean value calculated during said fixed time period;
   E. calculating the mean scattered intensity value at each angular location member of each of the two sets of angular directions;
   F. forming a mathematical average scattered intensity of each set by combining the individual mean intensities of each element of the set yielding two characterizing values;
   G. exposing for a fixed period of time the sample of said microparticles to the test environment;
   H. repeating steps B through F to yield two averaged values characterizing the microparticle ensemble after exposure to the test environment after the fixed period of time;
   I. calculating a response of the microparticles to their environment by forming a functional combination of the two values obtained from step F with the two values obtained from step M.

11. The process of claim 10 where the scattered intensities are measured by detectors lying in a plane.

12. A process for measuring the presence of a particular environmental factor capable of changing the two characterizing values of a set of test microparticles comprising the steps of:
   A. preparing a test sample that could contain the environmental factor sought;
   B. preparing a control sample known to be free of the environmental factor sought;
   C. Adding to each of the samples of steps A and B an equal aliquot of microparticles known to be responsive to the environmental factor sought:
   D. performing the measurement of claim 8 to yield the response of the microparticles to the test and control environments of steps A and B, respectively;
   E. comparing the responses so obtained to deduce that
      (i) if the responses are the same, the test sample did not contain a sufficient amount of environmental factor sought to yield a response difference, or
      (ii) if the responses are different, the test sample did contain a sufficient amount of environmental factor sought to yield a response difference.

13. The process of claim 12 where the environmental factor is a toxicant or chemical agent.

14. The process of claim 12 where the microparticles are bacteria;

15. The process of claim 12 where test sample is prepared from an exudate of a food specimen suspected of containing a chemical agent.

16. The process of claim 10 where the incident radiation is produced by a laser at visible or infrared optical wavelengths.

17. The process of claim 10 where said mathematical average scattered intensity V of each set containing n intensity values is of the form $$V = \frac{1}{n} \sum_{i=1}^{n} W(I_i) f_i,$$

where W is a function of the intensity $I_i$ measured at angular location i and $f_i$ is a weighting factor associated with said measured value $I_i$.

18. The process of claim 10 where the response, R, of the microparticles to their environment is calculated from an expression of the form $$R = a(V_{10} - V_{1t}) + b(V_{20} - V_{2t}) + c(m_o - m_t),$$

where a, b, and c are constants, $V_{10}$ and $V_{20}$ are the two characterizing values calculated at time zero before exposure of the said microparticle ensemble to the environment, $V_{1t}$ and $V_{2t}$ are the two characterizing values calculated after the ensemble has been exposed to the environment for at time ti, $m_0 = (V_{20} - V_{10})/\Delta\Theta$, $m_t = (V_{2t} - V_{1t})/\Delta\Theta$, $\Delta\Theta = \Theta_2 - \Theta_1$, and $\Theta_1$ and $\Theta_2$ are the two angular locations about which the scattered intensities are measured.

19. The process of claim 10 where the microparticles are bacteria and the environment is an antimicrobial.

20. The process of claim 19 whereby the measurements are performed over a range of time intervals such that the two characterizing values of the sample evolve in time to yield the characterizing properties of the microparticles whose detection is sought.

21. The process of claim 20 where the evolving particles are bacteria or yeasts and the sample is blood or urine.

22. The process of claim 10 where the microparticles are antigens and the environment is a solution of specific antibodies.

23. An apparatus to determine two scattering values characteristic of a microparticle ensemble comprising:
   A. means to produce a collimated beam of radiation;
   B. means to hold a sample in this beam, said sample containing the microparticle ensemble;
   C. means to detect and collect radiation at two sets of angular locations each subtending a specific angle measured with respect to the direction of the incident beam;
   D. means to control the period of time during which scattered radiation is detected by said detectors;
   E. means to convert said detected values into digital representations and means to store said digital representations;
   F. means to analyse said stored digital values and suppress those values arising from spurious elements/noise of said microparticles ensemble;
   G. means to obtain an average scattered intensity value for each angular location of each of said detectors;
   H. means to calculate a weighted and averaged sum of all stored and processed digital values for each set yielding a single characterizing value for each of said two sets, said two values characteristic of detected, and weighted, and averaged scattered intensities at each of the two said principal angular locations.

24. The apparatus of claim 23 where the collimated beam of radiation is from a laser at visible or infrared wavelengths.

25. The apparatus of claim 23 where the means to collect radiation all lie in a plane.

26. The apparatus of claim 25 where the radiation is vertically polarized with respect to the plane containing said means to collect radiation.

27. The apparatus of claim 23 where the means of D, F, G and H is a computer.

28. The apparatus of claim 23 where the means to collect radiation are placed on a circular arc about the scattering ensemble of particles equidistant therefrom.

29. The apparatus of claim 23 where the collection means have a mask limiting thereby the radiation incident on each.

30. The apparatus of claim 28 where the masks at smaller scattering angles are smaller than those at larger scattering angles.

31. The apparatus of claim 23 wherein the means to collect and detect radiation includes optical fibers.

32. The apparatus of claim 23 wherein the means to collect and detect radiation includes a multianode microchannel array tube.

33. The apparatus of claim 23 wherein the means to collect and detect radiation includes photodiodes.

34. The apparatus of claim 23 wherein the means to collect and detect radiation includes photomultiplier tubes.

* * * * *